(12) United States Patent
Jakoubek (10) Patent No.: US 10,664,004 B2
(45) Date of Patent: May 26, 2020

(54) ACTUATING ELEMENT AND A PAIR OF ROCKER UNITS FOR AN ACTUATING ELEMENT

(71) Applicant: Jakoubek Medizintechnik GmbH, Liptingen (DE)

(72) Inventor: Franz Jakoubek, Liptingen (DE)

(73) Assignee: JAKOUBEK MEDIZINTECHNIK GMBH, Liptingen (DE)

( * ) Notice: Subject to any disclaimer, the term of this patent is extended or adjusted under 35 U.S.C. 154(b) by 1518 days.

(21) Appl. No.: 14/231,160

(22) Filed: Mar. 31, 2014

(65) Prior Publication Data

US 2014/0311272 A1    Oct. 23, 2014

(30) Foreign Application Priority Data

Apr. 17, 2013    (EP) .................................... 13002016
Mar. 4, 2014     (EP) .................................... 14000764

(51) Int. Cl.
*G05G 7/00*    (2006.01)
*A61B 17/29*   (2006.01)

(52) U.S. Cl.
CPC ........... *G05G 7/00* (2013.01); *A61B 17/2909* (2013.01); *A61B 2017/2946* (2013.01); *G05G 2505/00* (2013.01); *Y10T 74/20396* (2015.01)

(58) Field of Classification Search
CPC .... A61B 2017/2946; A61B 2017/2919; G05G 7/00
See application file for complete search history.

(56) References Cited

U.S. PATENT DOCUMENTS

| 5,501,698 | A | * | 3/1996 | Roth | A61B 17/1285 606/174 |
| 5,618,306 | A |   | 4/1997 | Roth et al. | |
| 6,322,578 | B1 | * | 11/2001 | Houle | A61B 17/2909 600/564 |
| 7,556,637 | B2 | * | 7/2009 | Dausch | A61B 17/1608 606/208 |
| 2008/0064929 | A1 | * | 3/2008 | Wiedenbein | A61B 17/2909 600/131 |
| 2010/0004677 | A1 | * | 1/2010 | Brostoff | A61B 17/2909 606/205 |
| 2017/0252053 | A1 | * | 9/2017 | Kaercher | A61B 17/29 |

* cited by examiner

*Primary Examiner* — Terence Boes
*Assistant Examiner* — Randell J Krug
(74) *Attorney, Agent, or Firm* — Shlesinger, Arkwright & Garvey LLP (57) ABSTRACT

An actuating element for actuating an instrument for performing minimally invasive interventions comprises a first handle half-shell and a second handle half-shell movable relative to each other and connected with each other at one end by a biasing mechanism; a tube arranged substantially centrally between the handle half-shells; a linkage mechanism arranged between the handle half-shells and the tube in order to transmit an actuating movement of the handle half-shells; a locking mechanism with a latching rocker arranged on the first handle half-shell and a locking rocker arranged on the second handle half-shell, wherein the two rockers enter into locking connection with each other through an opening provided therefor in the tube when the handle half-shells are moved together, and wherein the rockers are mounted around a pivot axis such that a swiveling or pivoting movement of the rockers lies within a plane defined by the handle half-shells.

11 Claims, 12 Drawing Sheets

Fig. 11D

ACTUATING ELEMENT AND A PAIR OF ROCKER UNITS FOR AN ACTUATING ELEMENT

TECHNICAL FIELD

The present invention relates to an actuating element as well as a pair of rocker units for an actuating element. In particular, the present invention relates to an actuating element for actuating an instrument for performing minimally invasive interventions which operatively interacts with a handle of the actuating element.

DESCRIPTION OF THE STATE OF THE ART

Actuating elements of this generic type are known. For example, US 2010/0004677 A1 discloses an actuating element comprising two handle half-shells that can be moved relative to each other, wherein the two handle half-shells are connected together at one end by a pretensioning or biasing mechanism and a tube is provided essentially in the middle between the two handle half-shells. In order to transmit an actuating movement of the handle half-shells, a linkage mechanism arranged between the handle half-shells and the tube is provided, the linkage mechanism being operatively connected to a rod running inside the tube. A similar configuration is also known from DE 102 93 222 B4. Further, U.S. Pat. No. 6,322,578 B1 discloses an actuating element comprising two handle half-shells that can be moved relative to each other. The known actuating element comprises two rocker units (catches) that are engaged upon actuation of the two handle half-shells and that can engage in a snappingly manner with each other. Each rocker unit is positioned in a respective handle half-shell such that upon closure of the handle half-shells they engage with complementary snap-in elements. Upon meeting of the snap-in elements, the two handle half-shells edge each other away around an axis generally parallel to the central tube axis, resulting in a swiveling movement of the handle half-shells transverse to the extension of the handle half-shells.

SUMMARY OF THE INVENTION

By contrast, according to the invention, an actuating element having the features as disclosed herein, are proposed.

Thus, the actuating element of the invention has a locking or snap-in mechanism that permits the actuating element to be locked when the handle half-shells are moved or squeezed together.

The locking mechanism comprises a latching or snap-in rocker arranged on a first handle half-shell and a locking rocker arranged on a second handle half-shell. When the handle half-shells are moved together, these two rockers enter into a locking connection with each other, through an opening in the tube provided for this purpose.

In one possible embodiment, provision is made for both rockers to be released from the locking connection by renewed actuation of the handle half-shells while these are in the together position.

In a further possible embodiment, the locking rocker is provided with a locking element and the latching rocker is provided with an undercut that can be brought into operative interaction with the locking element on the locking rocker.

The locking rocker and/or the latching rocker may each comprise a set screw or adjusting screw.

Further advantages and embodiments of the invention may be derived from the description and the attached drawing.

It is apparent that the aforementioned features, and those which are still to be mentioned below, may be used not only in the respectively stated combination, but also in other combinations or also by themselves, without departing from the scope of the present invention.

The invention is schematically illustrated in the drawing by an exemplary embodiment, and it will be described in detail below, with reference to the drawing.

DETAILED DESCRIPTION OF THE INVENTION

In the Figures, like elements and also elements having the same function are depicted with the same reference numerals.

Figure 1:
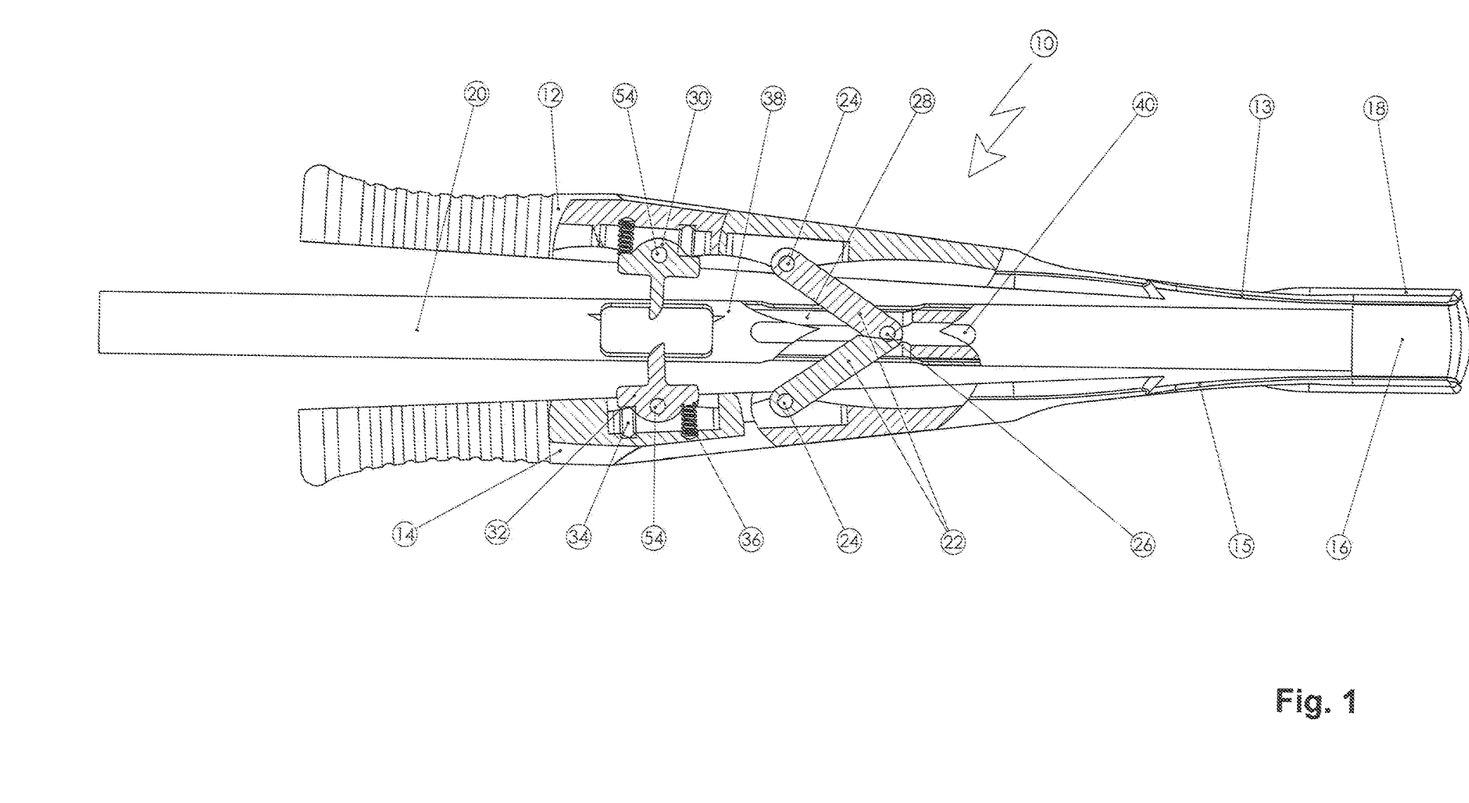
FIG. 1 shows a lateral partial sectional view of a first exemplary embodiment of an actuating element according to the invention.

FIG. 1 shows a lateral partial sectional view of an actuating element 10 according to the invention for actuating an instrument that operatively interacts with the handle to perform minimally invasive surgical interventions. For the sake of simplifying the drawing and for greater clarity, only the actuating element itself is shown. The instrument used for minimally invasive interventions (which could be, for example, a clamp, forceps, scissors, or similar) is not illustrated. The connection between the instrument and the actuating element is made in a manner known to a person skilled in the art.

The actuating element 10 according to the invention comprises two handle portions 12, 14 (called handle half-shells in the context of this application) which at one end (13, 15) are connected with each other via a pretensioning or biasing mechanism. In the exemplary embodiment illustrated, the pretensioning mechanism comprises a shaft receptacle 16 with a gripping spring 18. The handle half-shells may be formed integrally with the shaft receptacle or the biasing mechanism, respectively. This measure allows the manufacture and diminishes friction between the parts during use and also reduces mechanical wearout. The handle spring may, as appropriate, be formed integrally with the biasing mechanism.

A tube 20 is arranged substantially in the middle between the two handle half-shells 12, 14, said tube serving, in principle in a known manner, to transmit an actuating movement of the handle half-shells 12, 14. A linkage mechanism comprising a pair of articulated or linkage arms 22 is provided for transmitting this relative movement of the handle half-shells 12, 14, said articulated arms pivoting at one end respectively around a rivet 24 on one of the two handle half-shells 12, 14, and at the other end around a common pivoting point (or pivot axis), namely a pin 26 on a sliding element 28 guided in the tube 20. For this purpose, an axial slot 40 is provided in the tube 20.

Furthermore, the actuating element 10 according to the invention comprises a locking mechanism allowing the actuating element 10 to be arrested or locked when the handle half-shells 12, 14 are squeezed together.

The snap-in or locking mechanism according to the invention comprises a latching rocker 30 arranged on a first handle half-shell 12, as well as a locking rocker 32 arranged on a second handle half-shell 14. The two rockers 30, 32 enter into contact with each other through an opening 38 provided therefor in the tube 20 when the handle half-shells 12, 14 are moved together. The two rockers 30, 32 are designed in such a way that when they make contact they snappingly interlock with each other and thus prevent the pretensioned/biased handle half-shells 12, 14 from moving apart again, such that the handle half-shells 12, 14 are locked in this position.

When renewed pressure is applied to the handle half-shells 12, 14, the interlocking of the two rockers 30, 32 is released such that the handle half-shells 12, 14 can return to their starting position (shown in the Figure) under the action of the pretensioning.

The two rockers 30, 32 may be designed, for example, in such a manner that one of the rockers 30 possesses an undercut which, when contact is made with the other rocker 32, locks into a locking element provided thereon. The locking element can, for example, be a locking nose or snap-in nose.

As can be seen in the Figure, the two rockers 30, 32 are suitably pivotably arranged on a respectively assigned handle half-shell. To this end, the two rockers 30, 32 are pivotally arranged around a pivot axis 54. As can be seen readily from FIG. 1, the pivot axis 54 extends perpendicular to the drawing plane and thus substantially perpendicular to a longitudinal axis of the tube 20. This results in a swiveling movement of the two rockers 30, 32 in a plane that is spanned or generated by the two handle half-shells 12, 14.

For biasing the two rockers, pressure springs 36 are provided, respectively, as well as grub screws or threaded pins 34 for adjustment purposes. Each pressure spring 36 and grub screw 34 are arranged on opposite sides of the respective rocker pivot axis. This arrangement of the spring 36 outside of the rocker body, as it can be recognized from the depiction of the Figure very easily, allows for a more sensitive, i.e. more accurate adjustment of the rocker biasing and thus the rocker locking force. As a result, the fine tuning is enhanced. The use of a (inexpensive) pressure spring instead of a torsion spring supports this as the pressure spring exercises its force in a more constant manner than the torsion spring which thus allows for a more sensitive actuation.

Figure 2A:
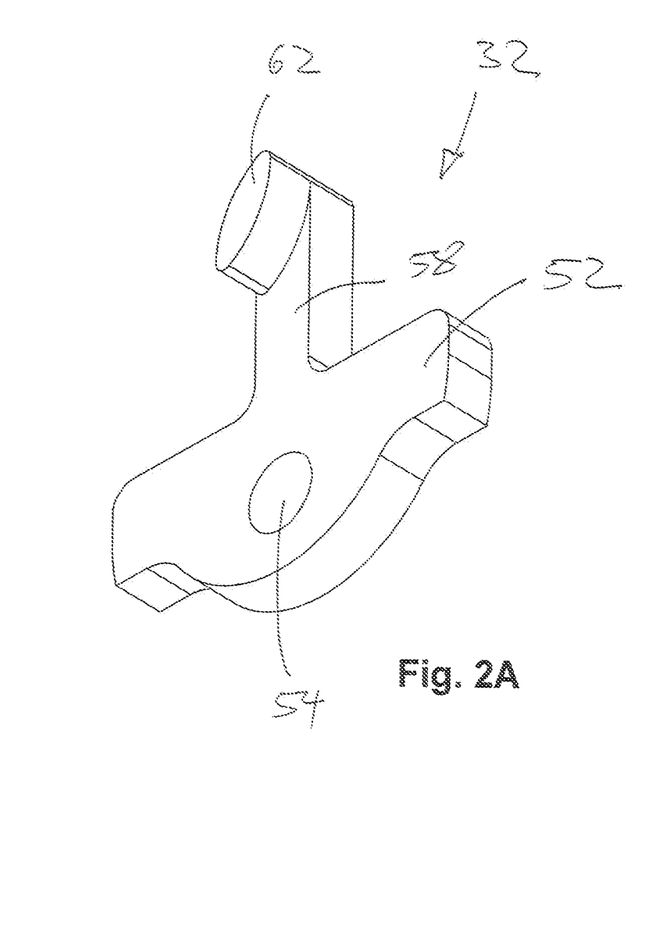
FIG. 2A shows a perspective view of a locking rocker according to the invention.
Figure 2B:
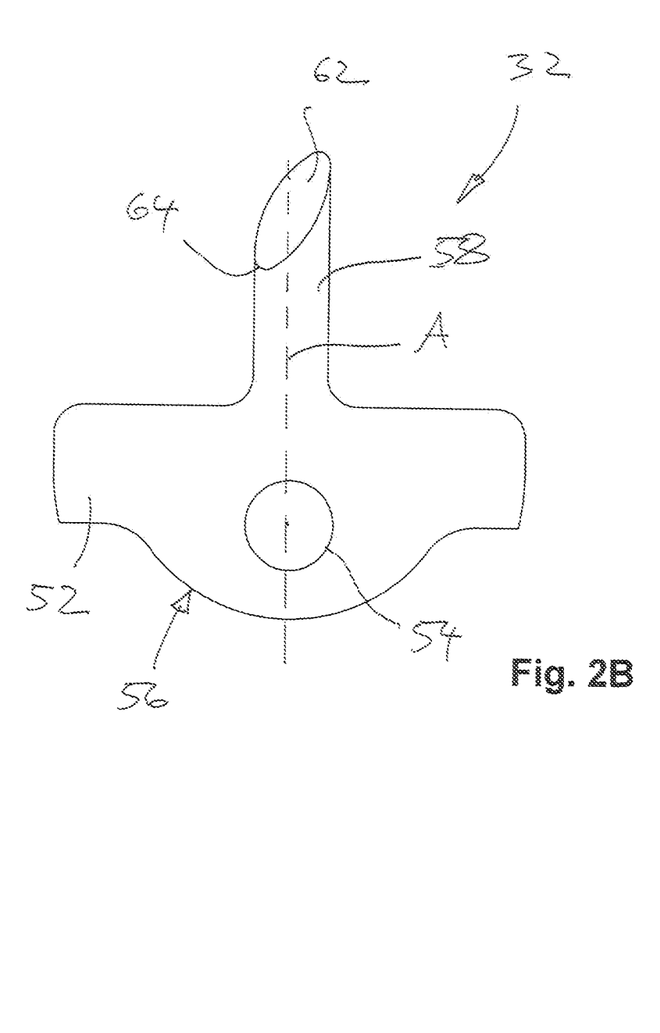
FIG. 2B shows a lateral plan view of the locking rocker of FIG. 2A.
Figure 3A:
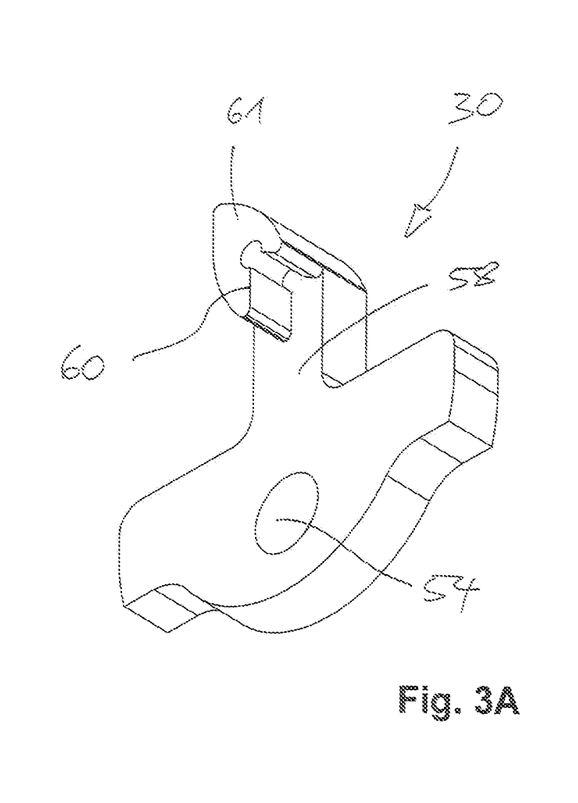
FIG. 3A shows a perspective view of a latching rocker according to the invention.
Figure 3B:
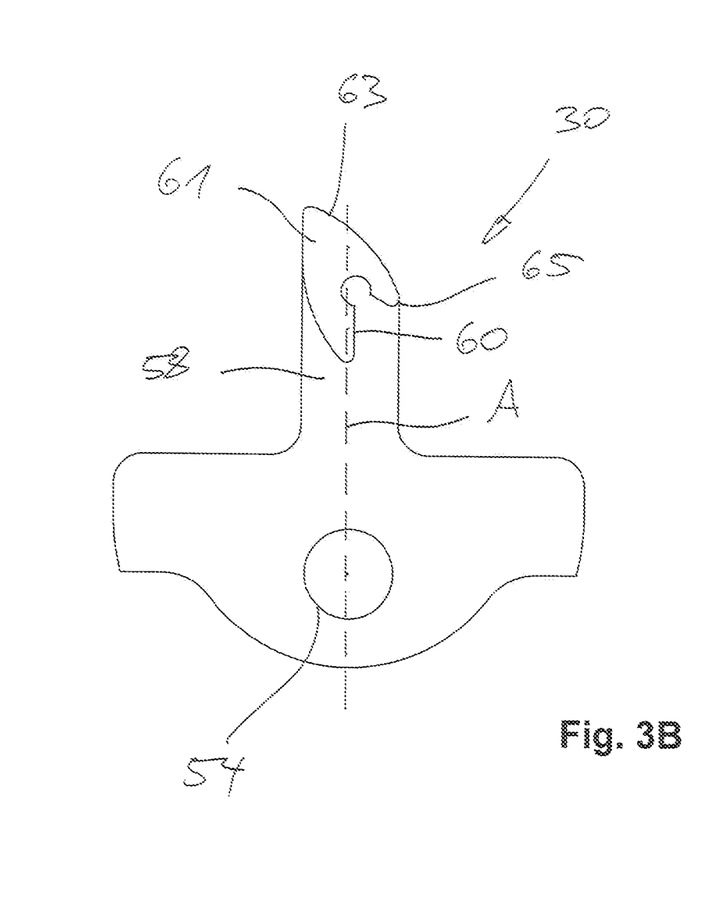
FIG. 3B shows a lateral plan view of the latching rocker of FIG. 3A.
Figure 4A:
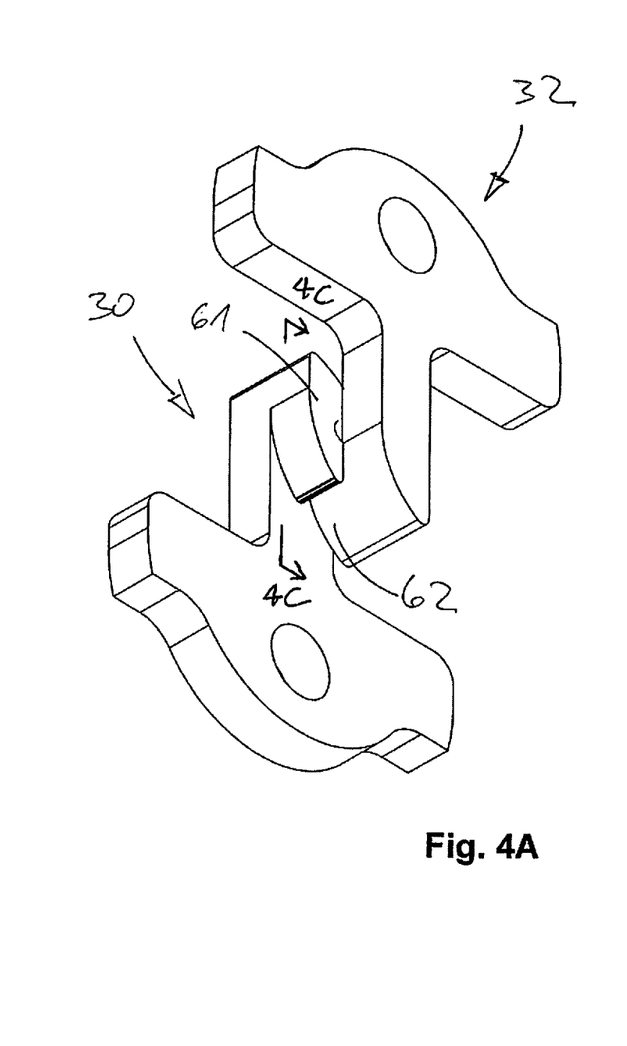
FIG. 4A shows a perspective view of the rockers of FIGS. 2A and 3A in the engaged or interlocked position.
Figure 4B:
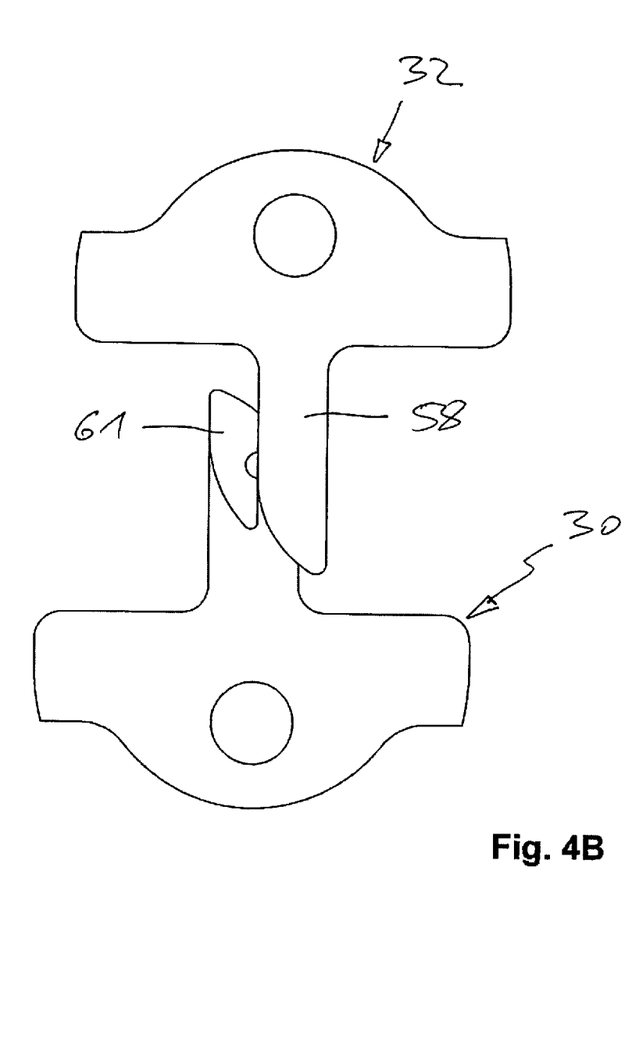
FIG. 4B shows a lateral plan view of the interlocked position of FIG. 4A.
Figure 4C:
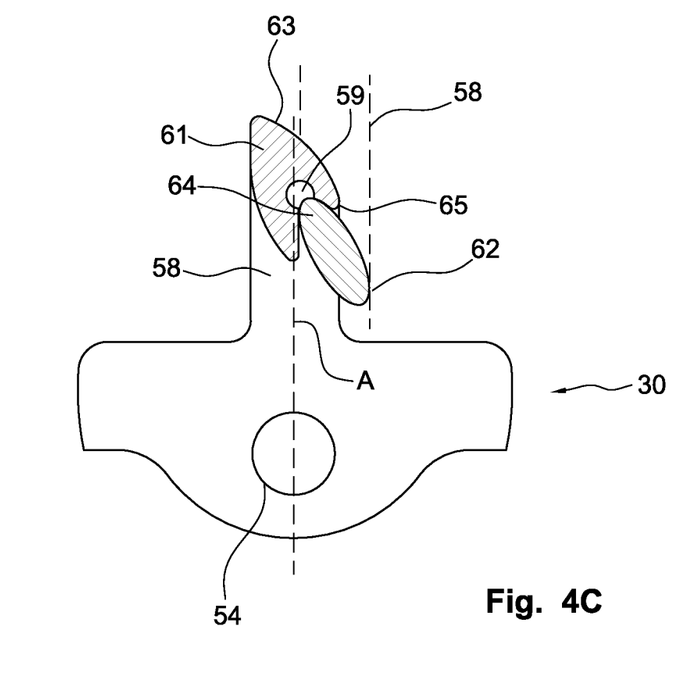
FIG. 4C is a cross-sectional view through line 4C-4C in FIG. 4A.

The two rockers 30, 32 according to the invention are illustrated in more detail in FIGS. 2 to 4.

FIG. 2A shows a perspective view and FIG. 2B a lateral plan view of a locking rocker 32 according to the invention. Correspondingly, FIG. 3A shows a perspective view and FIG. 3B a lateral plan view of a latching rocker 30 according to the invention.

Both rockers 30, 32 each comprise a rocker body 50 or 52 having a central borehole through which passes the pivot axis 54. The two rocker bodies 50, 52 are substantially equal in design and particularly, each has a cam-shaped side 56. The cam shape 56 facilitates the guidance of the rocker. On both sides of the cam curving, shoulders are formed. A first of these shoulders serves for engagement with the pressure spring 36 (cf. FIG. 1 as well as the embodiments of FIGS. 8 and 9). The opposing second shoulder serves, in the case of the embodiment of FIG. 1, for engagement with the threaded pin 34.

On the side opposite the cam-shaped side 56 each rocker 50, 52 has a rocker neck 58. The operative locking or snap element of the respective rocker is located at the end of each rocker neck 58 distal from the rocker.

On its rocker neck 58 the locking rocker 32 has a locking element 62. The locking element 62 projects from the rocker neck 58 in a direction perpendicular to the axis of elongation A of the latter. The locking element 62 has an essentially oval shape, the main axis of which is inclined in relation to the axis of elongation. The angle of inclination can be for example 15° or 30° or 45° (measured clockwise in the depiction shown in the Figures). Other angles of inclination are also possible and are obvious to the person skilled in the art from his understanding of the present disclosure.

On its rocker neck 58 the latching rocker 30 has an element 61 having an undercut 60. The element 61 projects from the rocker neck 58 in a direction perpendicular to the axis of elongation A. The element 61 has a substantially oval shape, the main axis of which is inclined in relation to the angle of elongation. The angle of inclination is selected to correlate with the angle of inclination of the locking element 62 of the locking rocker 32 and may, for example, be 15° or 30° or 45° (measured in the counter-clockwise direction in the depiction shown in the Figures).

The undercut 60 is provided on the oval shape of the element 61 such that it points in the direction of the rocker body 56 and is suitable for receiving a tip 64 of the oval locking element 62, said tip pointing towards the rocker body 56 of the locking rocker 32. When the opposed pivotally arranged rockers 30, 32 approach each other, the said tip 64 of the locking element 62 comes into contact with the element 61 of the latching element 30 at an oval surface 63 distal from the rocker. The two rockers then push each other aside, so that they pivot around their respective pivot axes 54, and the tip 64 slides along the surface 63, then around an edge 65 of the undercut 60, where it slips into the undercut 60 and engages therein. This interlocking position is illustrated, by way of example, in FIGS. 4A, 4B and 4C.

As already described above, the two rockers 30, 32 are unlocked again by applying renewed pressure to the handle half-shells 12, 14 so that, under the action of the pretensioning, the latter return to their starting position. The described swiveling of the two rockers in the plane spanned by the two handle half-shells, as can be seen easily in the Figures, has the advantage that no transverse movement of the rockers transverse to this plane occurs, as it is known from the prior art, thus avoiding according transverse forces which can disturbingly occur in the use of the actuation element of the prior art. The actuation element of the invention can thus be used in a more precise manner as no transverse pressure forces onto the handle are present any longer.

Figure 5A:
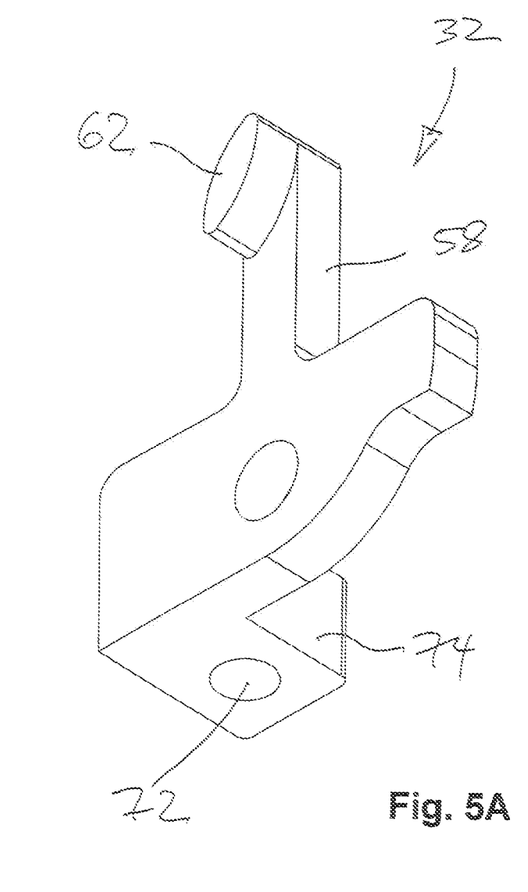
FIG. 5A shows a perspective view of a locking rocker according to the invention, with a set screw.
Figure 5B:
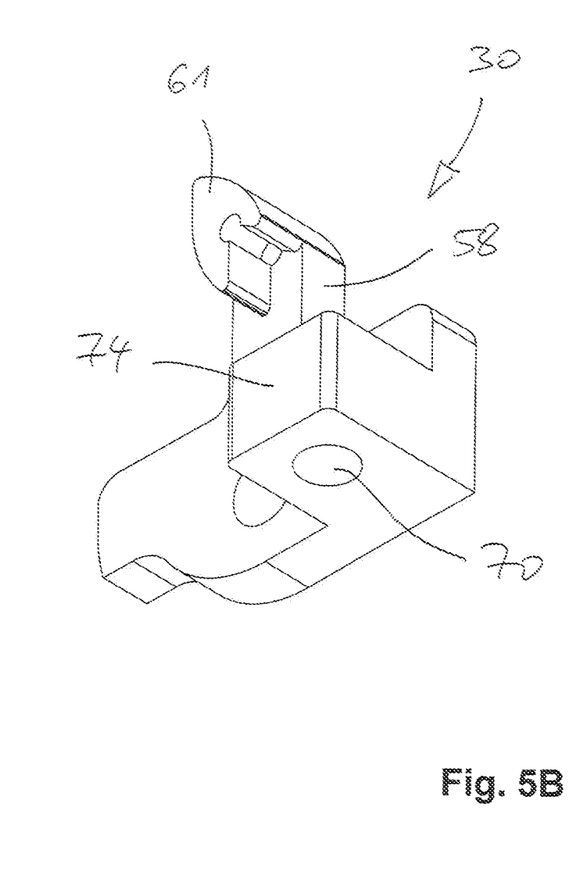
FIG. 5B shows a perspective view of a latching rocker according to the invention, with an adjusting screw.

FIGS. 5A and 5B show embodiments of the two rockers 30, 32 having projections 74, each having a threaded borehole 70, 72, which are suitably designed to receive set screws (not shown). The threaded boreholes 70, 72 run essentially parallel to the axis of elongation A of each rocker 30, 32 and essentially perpendicular to the pivot axis of each rocker 30, 32. By means of the set screws it is possible to adjust the positioning of each rocker so that the tip 64 of the locking element 62 comes into contact with the element 61 of the latching rocker at the desired point and the two rockers are correctly interlocked so that the subsequent unlocking can take place immediately without any complications or snagging occurring. Similar rockers according to the invention are shown in FIGS. 10A to 10D, the rocker bodies 50, 52 of which are designed more slender or narrow.

As can be seen easily from the FIGS. 3A, 3B, and 5B the undercut 60 of the oval element 61 has a hole 59 or bore in its inner apex end. The hole 59 can—as in the shown embodiment—be substantially circular. The axis of the hole 59 extends substantially parallel to the pivot axis 54. The hole 59 is made such that the end 64 of the engaging element 62 can be received therein. This hole 59 ensures that the two engaging elements 61, 62 of the two rockers 30, 32 do not disengage and move apart from each other in their locked position on their own, i.e. without renewed actuation of the rockers by means of the handle half-shells. Or in other words, the hole 59 minimizes the risk of unintentional disengaging of the rocker locking.

Figure 6:
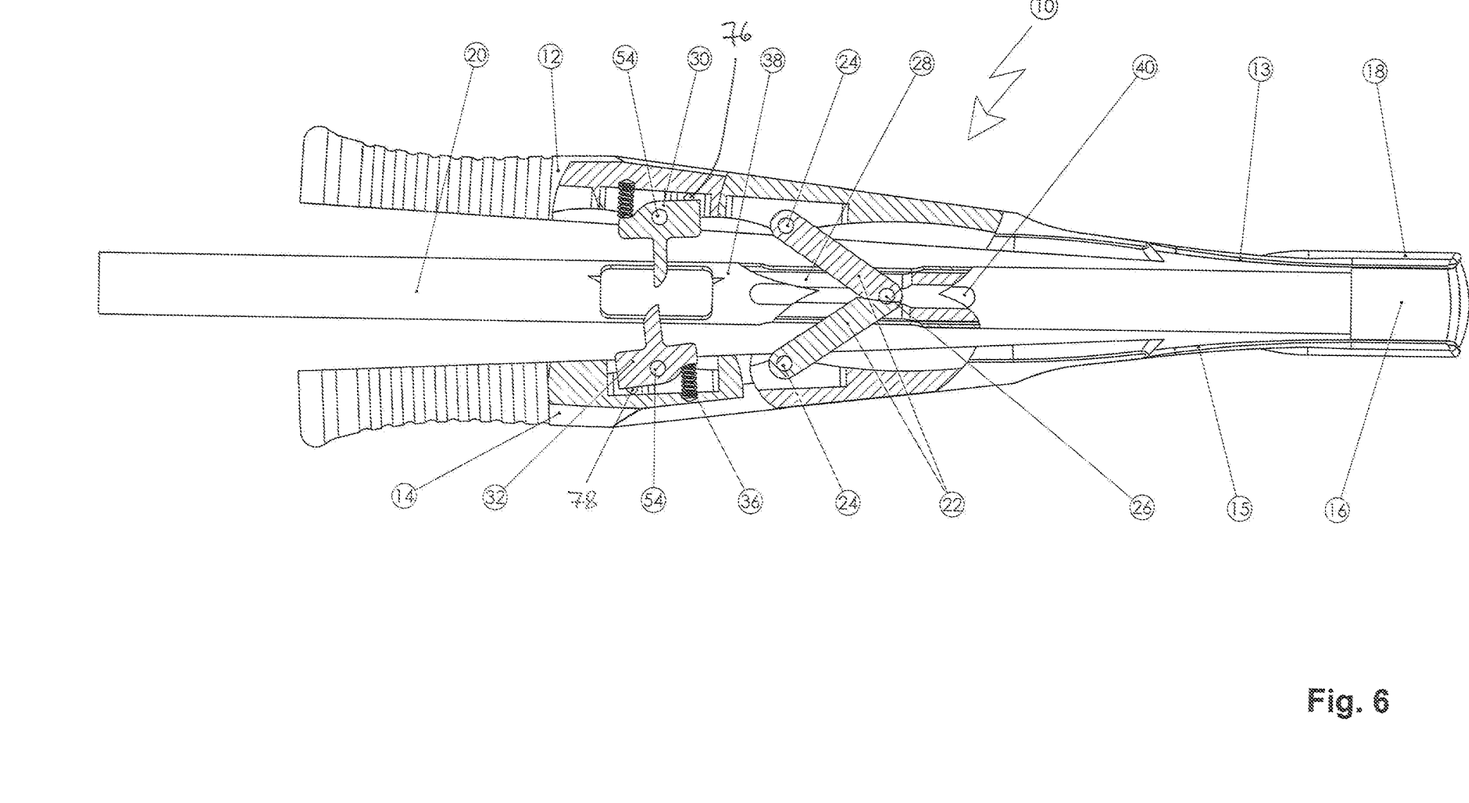
FIG. 6 shows a lateral partial sectional view of a further exemplary embodiment of an actuating element according to the invention, with the rockers of FIGS. 5A and 5B.
Figure 7A:
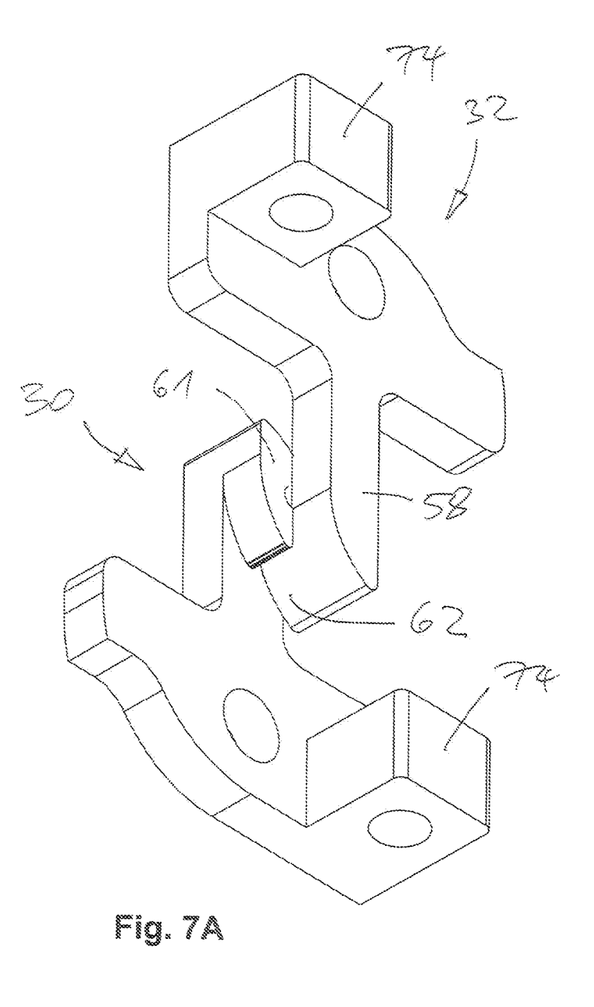
FIG. 7A shows a perspective view of the rockers of FIGS. 5A and 5B in the engaged or interlocked position.
Figure 7B:
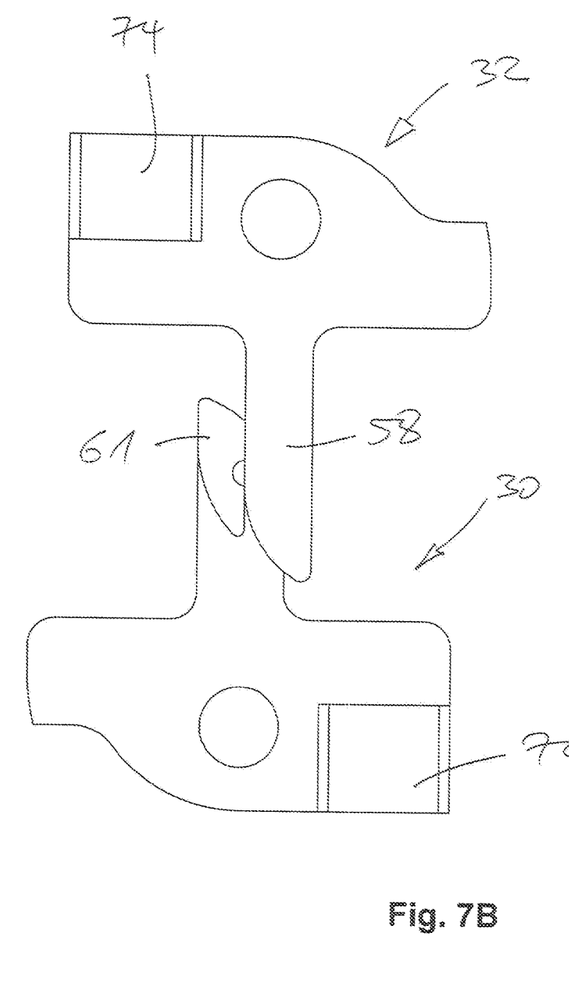
FIG. 7B shows a lateral plan view of the interlocked position of FIG. 7A.

Analogously to FIG. 1, FIG. 6 shows a lateral partial sectional view of an embodiment of an actuating element 10' according to the invention for actuating an instrument for performing minimally invasive interventions, said instrument being operatively interactive with the handle, and said actuating element having latching/locking rockers according to FIGS. 5A and 5B, with set screws 76 or 78 being provided in these rockers. The position of each rocker 30, 32, can be adjusted by how much the respective set screw 76 or 78 is screwed in.

Corresponding to the illustrations of FIGS. 4A and 4B, FIGS. 7A and 7B show the interlocking position of the latching/locking rockers of FIGS. 5A and 5B.

Figure 8:
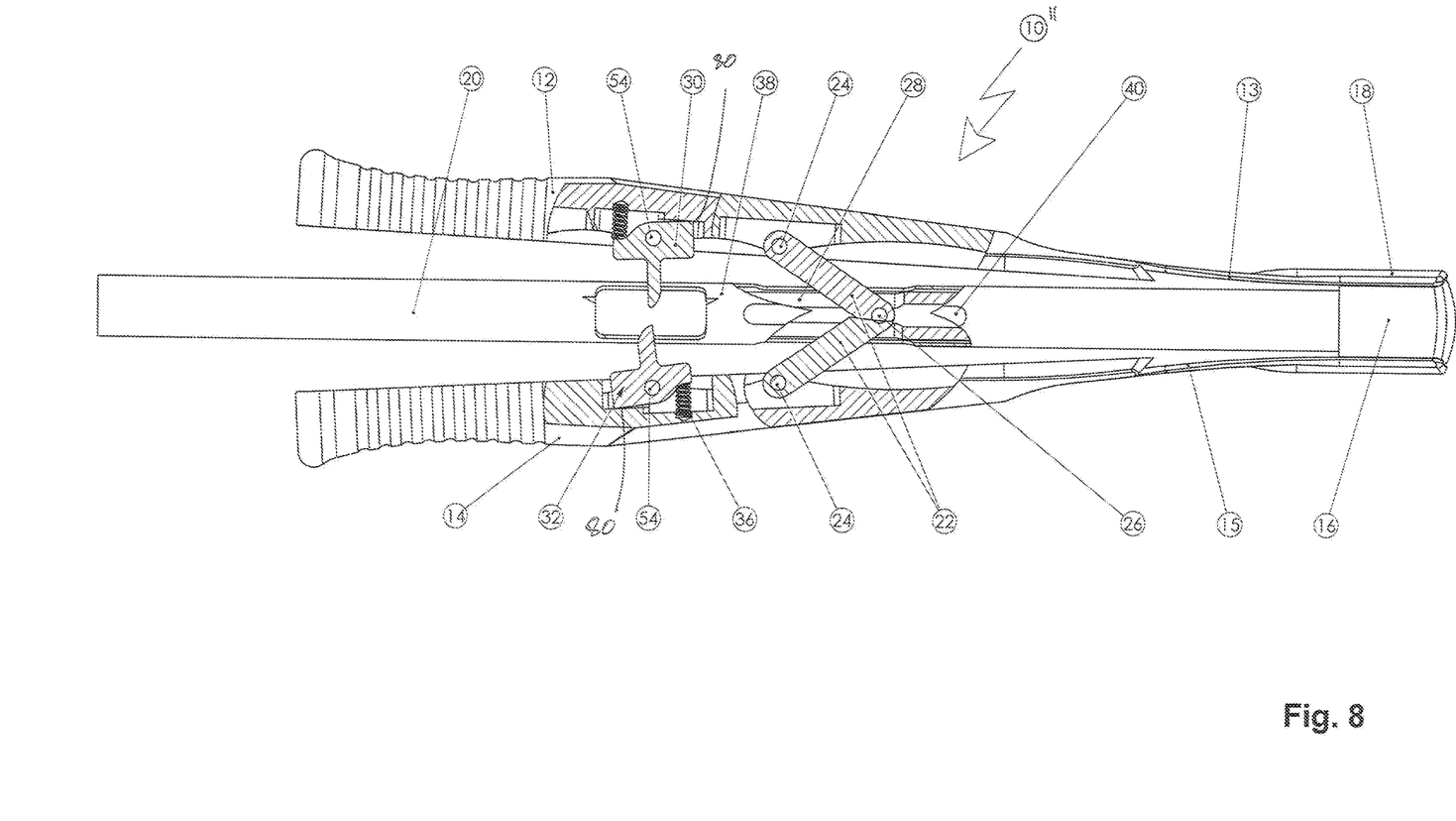
FIG. 8 shows a lateral partial sectional view of a third exemplary embodiment of an actuating element according to the invention.
Figure 9:
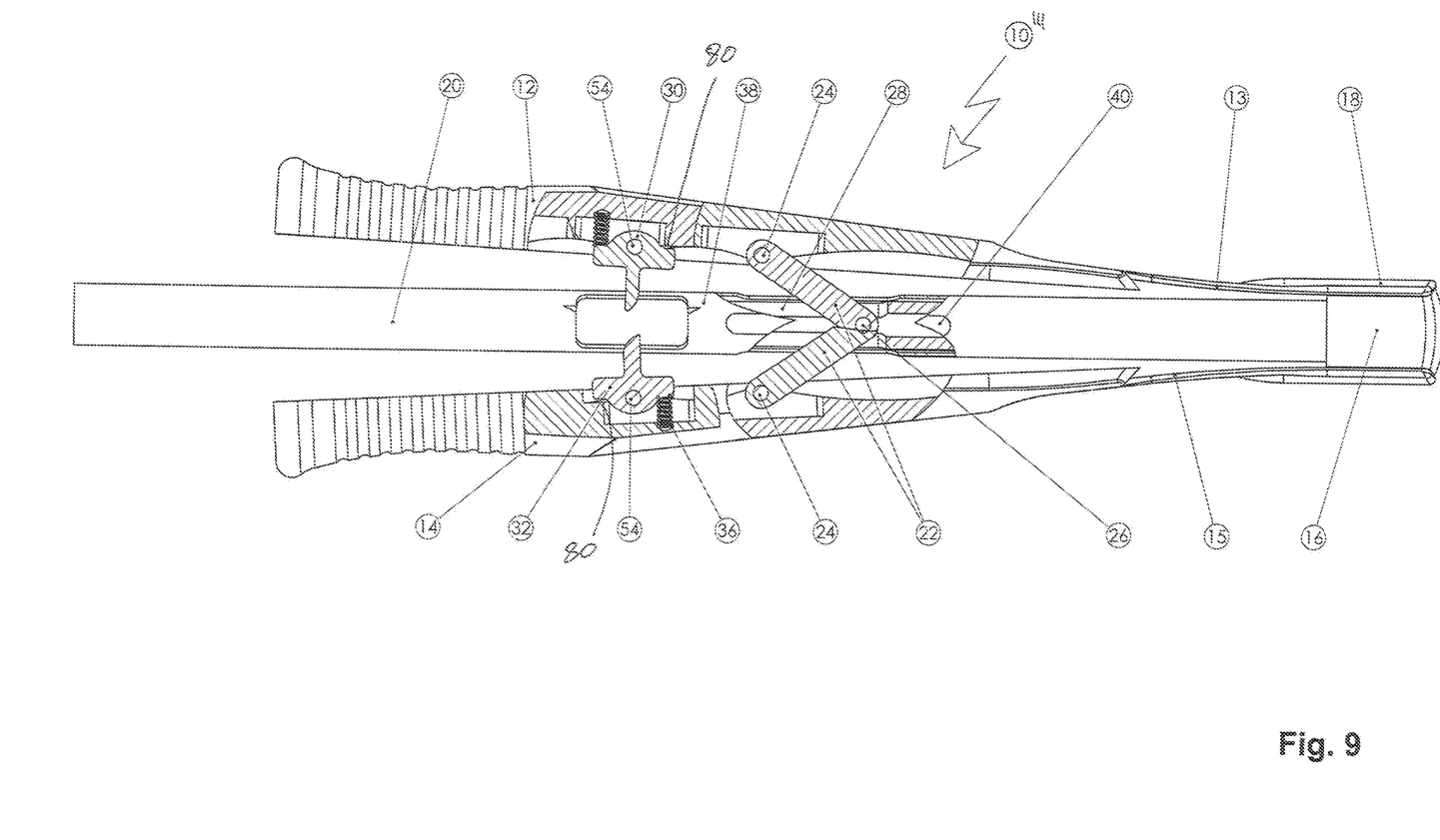
FIG. 9 shows a lateral partial sectional view of a fourth exemplary embodiment of an actuating element according to the invention.
Figure 10A:
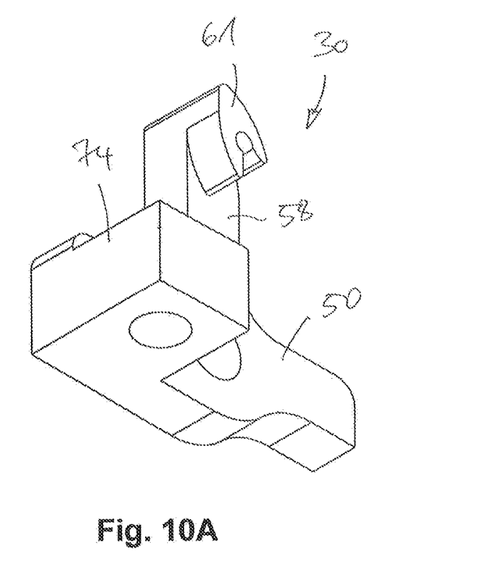
FIGS. 10A to 10D show a further exemplary embodiment of a rocker pair according to the invention, similar to the rockers shown in FIGS. 5A and 5B.
Figure 10B:
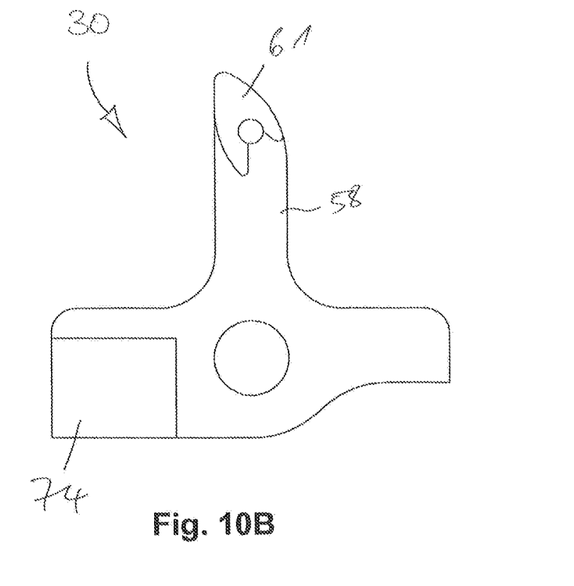
Figure 10C:
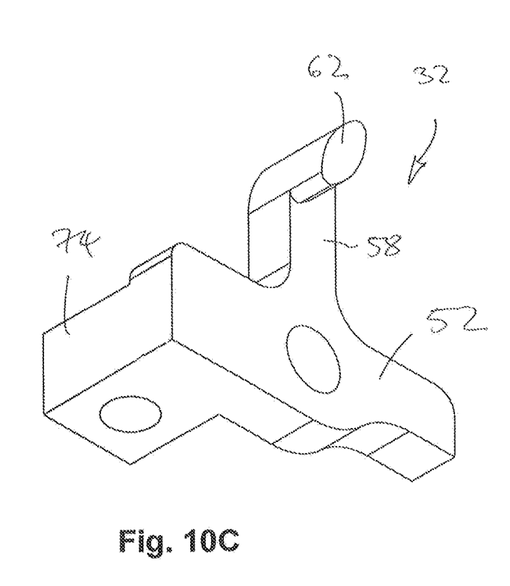
Figure 10D:
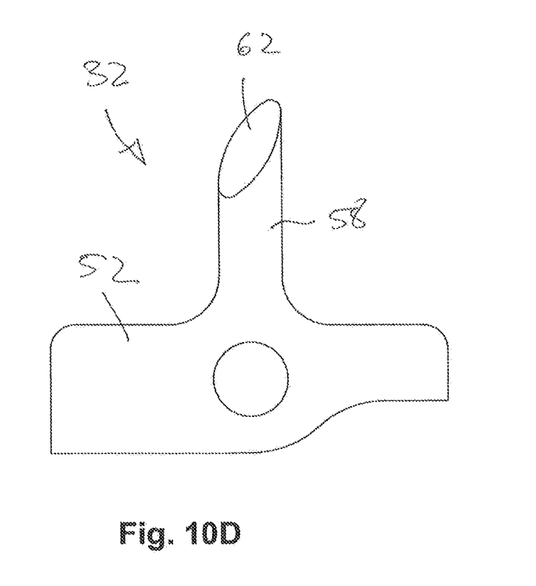
Figure 11A:
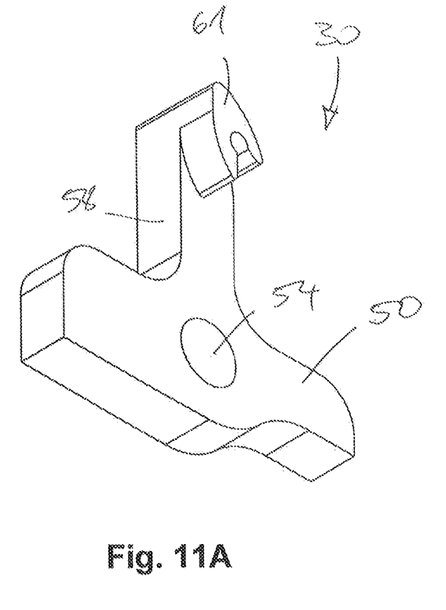
FIGS. 11A to 11D show a further exemplary embodiment of a rocker pair according to the invention, as installed in the actuating element of FIG. 8.
Figure 11B:
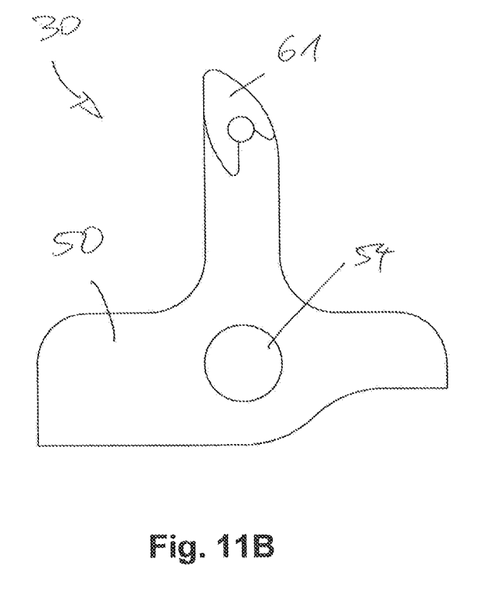
Figure 11C:
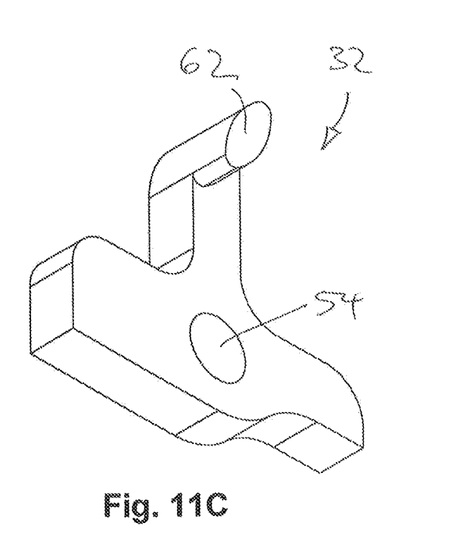
Figure 11D:
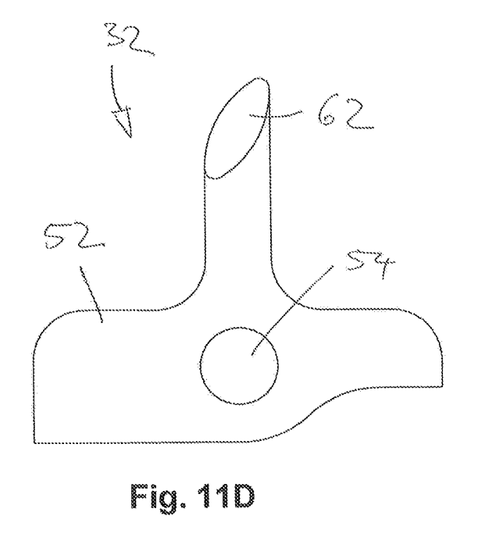

FIGS. 8 and 9 show lateral partial sectional views of two further embodiments of actuating elements 10" or 10''' respectively for actuating an instrument for performing minimally invasive interventions, said instrument being in operative interaction with the handle. In these two embodiments the respective edges of the latching/locking rockers 30, 32 opposite the biasing spring 36 rests on a shoulder 80 formed on the associated handle half-shell. The height of the shoulder 80 is matched to the shape of the rocker so that the desired alignment of each latching/locking rocker can be achieved. The rocker pair 30, 32 used in the actuating element 10" of FIG. 8 is shown enlarged and in more detail in FIGS. 11A to 11D.

I claim:

1. An actuating element for actuating an instrument for performing minimally invasive interventions, said instrument being operatively interactive with a handle, said actuating element, comprising:
   a first handle half-shell and a second handle half-shell, said first and second handle half-shells being movable relative to each other and connected with each other at one end by a biasing mechanism;
   a tube arranged substantially centrally between said first and second handle half-shells;
   a linkage mechanism arranged between said first and second handle half-shells and said tube in order to transmit an actuating movement of said first and second handle half-shells;
   said actuating element further comprising a locking mechanism with a latching rocker arranged on said first handle half-shell and a locking rocker arranged on said second handle half-shell, wherein said latching rocker and said locking rocker enter into locking connection with each other through an opening provided therefor in said tube when said first and second handle half-shells are moved together, and wherein said latching rocker and said locking rocker are mounted around respective pivot axes each being perpendicular to a longitudinal axis of said tube such that a swiveling or pivoting movement of said latching rocker and said locking rocker lies within a plane spanned by said first and second handle half-shells;
   wherein said latching rocker and said locking rocker each comprises a neck and first and second shoulders extending outwardly in opposite directions from said neck, at least one of said first and second shoulders acting as a stop for an adjusting spring or a threaded pin.

2. The actuating element according to claim 1, wherein said latching rocker and said locking rocker are released from their locking connection when said handle half-shells are moved together again.

3. The actuating element according to claim 1, wherein said locking rocker comprises a locking element, and said latching rocker comprises an undercut to be brought into operative interaction with said locking element of said locking rocker.

4. The actuating element according to claim 3, wherein said undercut comprises a bore or hole.

5. The actuating element according to claim 1, wherein said locking rocker and said latching rocker comprise an adjusting screw, respectively.

6. The actuating element according to claim 1, wherein said first and second handle half-shells each comprises a threaded pin assigned to said respective latching and locking rockers for fine alignment adjustment of said latching rocker and said locking rocker.

7. The actuating element according to claim 1, wherein said first and second handle half-shells each comprises a third shoulder assigned to said respective latching rocker and said locking rocker as a stop for said respective latching rocker and said locking rocker.

8. A pair of rockers for an actuating element for actuating an instrument for performing minimally invasive interventions, said instrument being in operative interaction with a handle, said pair of rockers comprising:

a latching rocker and a locking rocker, wherein said locking rocker comprises a locking element and said latching rocker comprises an undercut to be brought into operative engagement with said locking element of said locking rocker; and wherein said latching rocker and said locking rocker each comprises a neck and first and second shoulders extending outwardly in opposite directions from said neck, at least one of said first and second shoulders acting as a stop for an adjusting spring or a threaded pin.

9. The pair of rockers according to claim 8, wherein said locking rocker and said latching rocker each comprises an adjusting screw, respectively.

10. The pair of rockers according to claim 9, wherein said locking rocker and said latching rocker each comprises a projection with a threaded borehole, respectively, to house a set screw.

11. The pair of rockers according to claim 8, wherein said locking rocker and said latching rocker each comprises a pivot axis designed such that a pivoting movement of said locking rocker and said latching rocker when incorporated in an actuating element is effected substantially parallel to an axis of elongation of the actuating element.

\* \* \* \* \*